United States Patent [19]

Koszalka et al.

[11] Patent Number: 4,920,210
[45] Date of Patent: Apr. 24, 1990

[54] 2,6-DIAMINOPURINE-9-β-D-2',3'-DIDEOXYRIBOFURANOSIDE

[75] Inventors: George W. Koszalka, Apex; Thomas A. Krenitsky, Chapel Hill, both of N.C.

[73] Assignee: Burroughs Wellcome Co., Research Triangle Park, N.C.

[21] Appl. No.: 863,923

[22] Filed: May 15, 1986

[30] Foreign Application Priority Data

May 15, 1985 [GB] United Kingdom ............... 8512330

[51] Int. Cl.$^5$ ............................................ C07H 19/04
[52] U.S. Cl. ...................................... 536/24; 536/26
[58] Field of Search ................ 536/24, 26; 514/45, 514/26

[56] References Cited

U.S. PATENT DOCUMENTS 4,659,698  4/1987  Imbach et al. ................... 514/45

FOREIGN PATENT DOCUMENTS 0073795  6/1979  Japan ............................. 514/45

OTHER PUBLICATIONS

Chemical Abstracts, vol. 102, 1985, p. 19, Abstract No. 39565n.
Chemical Abstracts, vol. 90, 1979, p. 175, Abstract No. 198977y.
Chemical Abstracts, vol. 92, 1980, p. 49, Abstract No. 174458v.
Biochemistry, vol. 20, 1981, pp. 2628–2632, American Chemical Society, Columbus, Ohio.

*Primary Examiner*—Johnnie R. Brown
*Assistant Examiner*—Elli Peselev
*Attorney, Agent, or Firm*—Donald Brown

[57] ABSTRACT

The present invention relates to certain 2',3'-dideoxynucleosides and pharmaceutically acceptable derivatives thereof, methods for preparing them, their use in the treatment and prophylaxis of viral, especially retroviral, infections, and pharmaceutical formulations containing them.

1 Claim, No Drawings

2,6-DIAMINOPURINE-9-β-D-2',3'-DIDEOXYRIBOFURANOSIDE

The present invention relates to 2',3'-dideoxy-nucleosides, pharmaceutically acceptable derivatives thereof, and their use in therapy, particularly for the treatment or prophylaxis of certain viral infections.

In the comparatively new field of antiviral chemotherapy, few drugs exist which effectively combat the virus per se, owing to the difficulty of attacking the virus while leaving uninfected host cells unimpaired. It has recently been established that certain stages in the virus life-cycle, which vary from species to species, are specified by the virus itself. These stages may prove susceptible to attack where they differ sufficiently from any corresponding host-cell function. However, owing to great similarity between viral and host functions, effective treatments have proven very difficult to identify.

One group of viruses which has recently assumed a particular importance are the retroviruses. Retroviruses from a sub-group of RNA viruses which, in order to replicate, must first 'reverse transcribe' the RNA of their genome into DNA ('transcription' conventionally describes the synthesis of RNA and DNA). Once in the form of DNA, the viral genome is incorporated into the host cell genome, allowing it to take full advantage of the host cell's transcription/translation machinery for the purposes of replication. Once incorporated, the viral DNA is virtually indistinguishable from the host's DNA and, in this state, the virus may persist for as long as the cell lives. As it is virtually invulnerable to attack in this form, any treatment must be directed at another stage of the virus life cycle and will, of necessity, have to be continued until all virus-infected cells have died.

HTLV-I and HTLV-II are both retroviruses and are known to be causative agents of leukemia in man. HTLV-I infections are especially widespread and are responsible for many deaths world-wide each year.

A species of retrovirus has also been reproducibly isolated from patients with AIDS. While it has been extensively characterised, there is, as yet, no agreed name for the virus, and it is currently known either as human T-cell lymphotropic virus III (HTLV III), AIDS associated retrovirus (ARV), or lymphadenopathy associated virus (LAV). It is anticipated that the name to be agreed on internationally is acquired immune deficiency virus (AIDV). This virus (referred to herein as AIDV) has been shown preferably to infect and destroy T-cells bearing the OKT$^4$ surface marker and is now generally accepted as the aetiologic agent of AIDS. The patient progressively loses this set of T-cells, upsetting the overall balance of the immune system, reducing his ability to combat other infections, and predisposing him to opportunistic infections which frequently prove fatal. Thus, the usual case of death in AIDS victims is by opportunistic infection, such as pneumonia or virally induced cancers, and not as a direct result of AIDS infection.

Recently, AIDV has also been recovered from other tissue types, including B-cells expressing the T$^4$ marker, macrophages and non-blood associated tissue in the central nervous system. This infection of the central nervous system has been discovered in patients expressing classical AIDS symptoms and is associated with progessive demyelination, leading to wasting and such symptoms as encephalopathy, progressive dysarthria, ataxia and disorientation. Further conditions associated with AIDV infection are the asymptomatic carrier state, progressive generalised lymphadenopathy (PGL) and AIDS-related complex (ARC).

Reports have described the testing of compounds against various retroviruses, for example, Murine Leukaemia Virus (MuLV) a mouse retrovirus. M. A. Wagar et al. (J. Cell. Phys., 121 (1984) 402–408) found that the 2',3'-dideoxyribonucleosides of adenine, cytosine, thymine and guanine inhibited infections of cell-lines by MuLV, but no clear indication of therapeutic potential was given.

We have now discovered that 2',3'-dideoxynucleosides, as referred to below, are useful for the treatment or prophylaxis of viral infections, particularly retroviral infections and especially AIDS.

In a first aspect of the present invention, there is provided 2',3'-dideoxynucleosides having the following formula (I):

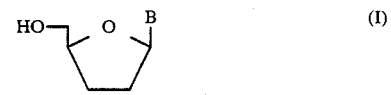

wherein B represents a purine base selected from 2,6-diaminopurine, 2-aminopurine, guanine, 6-methoxypurine and 6-methylthiopurine linked to the sugar residue at the 9-position, or a pharmaceutically acceptable derivative thereof, for use in the treatment or prophylaxis of a viral infection.

In vitro testing has shown that, with the exception of 2-aminopurine-9-β-D-2',3'-dideoxyribofuranside, the compounds according to the invention have particularly good activity against the following viruses: human T-cell lymphotropic viruses (HTLV), especially HTLV-I, HTLV-II and AIDV (HTLV-III); feline leukaemia virus, equine infectious anaemia virus and other lentiviruses, as well as other human viruses such as hepatitis B virus and Epstein-Barr virus (EBV). It will be appreciated that 2-aminopurine-9-β-D-2',3'-dideoxyribofuranoside is readily metabolized in vivo to 2',3'-dideoxyguanosine and is thus useful in the treatment of animals infected with the above-mentioned viruses. The invention accordingly provides the compounds according to the invention for use in the treatment or prophylaxis of any of the above infections.

Particularly good activity has been observed against those viruses which are retroviruses and also those DNA viruses which, like retroviruses, are incorporated into the host genome during their life-cycle, i.e. retrovirus-like DNA viruses. Thus, there is further provided the compounds according to the invention for use in the treatment or prophylaxis of retroviral, or retrovirus-like infections.

It will be appreciated that the compounds according to the invention may also be used in the manufacture of a medicament for the treatment or prophylaxis of any of the above-mentioned medical or veterinary indications.

By "a pharmaceutically acceptable derivative" is meant any pharmaceutically acceptable salt, ester, or salt of such ester, or any other compound which, upon administration to the recipient, is capable of providing (directly or indirectly) a 2',3'-dideoxynucleoside as described above, or an antivirally active metabolite or residue thereof.

Preferred esters of the compound of formula (I) include carboxylic acid esters in which the non-carbonyl moiety of the ester grouping is selected from straight or branched chain alkyl, alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy); sulphonate esters such as alkyl- or aralkylsulphonyl (e.g. methanesulphonyl); and mono-, di- or tri-phosphate esters.

Any reference to any of the above compounds also includes a reference to a pharmaceutically acceptable salt thereof.

With regard to the above-described esters, unless otherwse specified, any alkyl moiety present advantageously contains 1 to 18 carbon atoms, particularly 1 to 4 carbon atoms. Any aryl moiety present in such esters advantageously comprises a phenyl group.

Examples of pharmaceutically acceptable salts of the compounds of formula (I) and pharmaceutically acceptable derivatives thereof include base salts, eg derived from an appropriate base, such as alkali metal (e.g. sodium), alkaline earth metal (e.g. magnesium) salts, ammonium and $NX_4^+$ (wherein X is $C_{1-4}$ alkyl). Physiologically acceptable salts of an hydrogen atom or an amino group include salts of organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound of an hydroxy group include the anion of said compound in combination with a suitable cation such as $Na^+$, $NH_4^+$, and $NX_4^+$ (wherein X is a $C_{1-4}$ alkyl group).

Examples of formula (I) above include:

2′,3′-dideoxy-guanosine, 6-methylthiopurine-9-β-D-2′,3′-dideoxyribofuranoside, 6-methoxypurine-9-β-2′,3′-dideoxyribofuranoside, 2,6-diaminopurine-9-β-D-2′,3′-dideoxyribofuranoside and 2-aminopurine-9-β-D-2′,3′-dideoxyribofuranoside.

The present invention thus further provides the novel compounds of formula (I) wherein B represents a 2,6-diaminopurine, 6-methylthiopurine, 6-methoxypurine or 2-aminopurine base and their pharmaceutically acceptable derivatives, particularly for use in therapy.

Specific examples of pharmaceutically acceptable derivatives of the compound of formula (I) that may be used in accordance with the present invention include the monosodium salt and the following 5′ esters: monophosphate; disodium monophosphate; diphosphate; triphosphate; acetate; 3-methyl-butyrate; octanoate; palmitate; 3-chloro-benzoate; benzoate; 4-methyl-benzoate; hydrogen succinate; pivalate; and mesylate.

The compounds according to the invention, also referred to herein as the active ingredient, may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the infection and the chosen active ingredient.

In general a suitable dose will be in the range of 3.0 to 120 mg per kilogram body weight of the recipient per day, preferably in the range of 6 to 90 mg per kilogram body weight per day and most preferably in the range 15 to 60 mg per kilogram body weight per day. The desired dose is preferably presented as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Ideally, the active ingredient should be administered to achieve peak plasma concentrations of the active compound of from about 1 to about 75 μM, preferably about 2 to 50 μM, most preferably about 3 to about 30 μM. This may be achieved, for example, by the intravenous injection of a 0.1 to 5% solution of the active ingredient, optionally in saline, or orally administered as a bolus containing about 1 to about 100 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible for the active ingredient to be administered alone it is preferable to present it as a pharmaceutical formulation. The formulations of the present invention comprise at least one active ingredient, as above defined, together with one or more acceptable carriers thereof and optionally other therapeutic agents. Each carrier must be "acceptable" in the sense of being compatible with the other ingredients of the formulation and not injurious to the patient. Formulations include those suitable for oral, rectal, nasal, topical (including buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets preferably should be provided with an enteric coating to provide release in parts of the gut other than the stomach. This is particularly advantageous since the compounds of formula (I) are susceptible to acid hydrolysis.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and nonaqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

The compounds according to the invention may also be presented for use in the form of veterinary formulations, which may be prepared, for example, by methods that are conventional in the art. Examples of such veterinary formulations include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection e.g. as a sterile solution or suspension; or (when appropriate) by intramammary injection where a suspension or solution is introduced into the udder via the teat;

(c) topical application, e.g. as a cream, ointment or spray applied to the skin; or (d) intravaginally, e.g. as a pessary, cream or foam.

The administered ingredients may also be used in therapy in conjunction with other medicaments such as 9-[[2-hydroxy-1-(hydroxymethyl)ethoxy]methyl]guanine, 9-(2-hydroxyethoxymetyl)guanine (acyclovir), 2-amino-9-(2-hydroxyethoxymethyl)purine, interferon, e.g., α interferon, interleukin II, and phosphonoformate, or in conjunction with other immune modulating therapy including bone marrow or lymphocyte transplants or medications such as levamisol or thymosin which would increase lymphocyte numbers and/or function as is appropriate.

It should be understood that in addition to the ingredients particularly mentioned above the formulations of this invention may include other agents conventional in the art having regard to the type of formulation in question, for example, those suitable for oral administration may include such further agents as sweeteners, thickeners and flavouring agents.

2′,3′-Dideoxyguanosine is available from P. L. Biochemicals and may be prepared in conventional manner, e.g., as described in Prisbe et al, Synth. Commun. 1985, 15(5), 401–9. Other compounds according to the invention may be prepared in conventional manner, e.g., as described in the Examples.

The present invention further includes a process for the preparation of a compound of formula (I) and pharmaceutically acceptable derivatives thereof which comprises either:

(A) reacting a compound of formula:

(wherein B is as hereinbefore defined and R represents a precursor group for the hydroxy group, or for a pharmaceutically acceptable derivative group thereof) with an agent or under conditions serving to convert the said precursor group into the corresponding desired group; or (B) reacting a purine base of formula

(wherein B is as hereinbefore defined). or a functional equivalent thereof, with a compound serving to introduce the desired ribofuranosyl ring at the 9-position of the purine base of formula (III); and thereafter, or simultaneously therewith, effecting one or more of the folllowing optional conversions:

(i) when a compound of formula (I) is formed, converting it into a pharmaceutically acceptable derivative thereof, (ii) when a pharmaceutically acceptable derivative of a compound of formula (I) is formed, converting the said derivative into a compound of formula (I), or a different derivative thereof.

In the above-described process according to the invention, it will be appreciated that the precursor compounds of formula (II) as well as the above-mentioned agents and conditions, will be selected from those that are known in the art of nucleoside synthetic chemistry. Examples of such conversion procedures are described hereinafter for guidance and it will be understood that they can be modified in conventional manner depending on the desired compound of formula (I). In particular, where a conversion is described which would otherwise result in the undesired reaction of labile groups then such groups may be protected in conventional manner, with subsequent removal of the protecting groups after completion of the conversion.

With regard to process (A), R may represent a protected hydroxy group e.g. an ester grouping of the type referred to above in relation to formula (I) particularly acetoxy, or an ether group such as a trialkylsilyloxy group, e.g. t-butyldimethylsilyloxy or an aralkoxy group e.g. triphenylmethoxy. Such groups may be converted for example by hydrolysis to the desired hydroxy group or, by transesterification, to an alternative ester group.

With regard to process (B), this may be effected for example by treating an appropriate purine base of formula (III) or a salt or protected derivative thereof, with 2',3'-dideoxythymidine for example in the presence of purine nucleoside phosphorylase and thymidine phosphorylase, or 2'-deoxyribosyltransferase.

A compound of formula (I) may be converted into a pharmaceutically acceptable phosphate or other ester by reaction with respectively a phosphorylating agent, e.g. $POCl_3$ or an appropriate esterifying agent, e.g. an acid halide or anhydride. The compound of formula (I), including esters thereof, may be converted into pharmaceutically acceptable salts thereof in conventional manner, e.g. by treatment with an appropriate base. An ester or salt of a compound of formula (I) may be converted into the parent compound, e.g. by hydrolysis.

The following Examples are intended for illustration only and are not intended to limit the scope of the invention in any way. The term 'active ingredient' as used in the Examples means a compound of formula (I) or a pharmaceutically acceptable derivative thereof.

EXAMPLE 1: Tablet Formulations

The following formulations A and B are prepared by wet granulation of the ingredients with a solution of povidone, followed by addition of magnesium stearate and compression.

Formulation A

| | | mg/tablet | mg/tablet |
|---|---|---|---|
| (a) | Active ingredient | 250 | 250 |
| (b) | Lactose B.P. | 210 | 26 |
| (c) | Povidone B.P. | 15 | 9 |
| (d) | Sodium Starch Glycollate | 20 | 12 |
| (e) | Magnesium Stearate | 5 | 3 |
| | | 500 | 300 |

Formulation B

| | | mg/tablet | mg/tablet |
|---|---|---|---|
| (a) | Active ingredient | 250 | 250 |
| (b) | Lactose | 150 | — |
| (c) | Avicel PH 101 | 60 | 26 |
| (d) | Povidone B.P. | 15 | 9 |
| (e) | Sodium Strach Glycollate | 20 | 12 |
| (f) | Magnesium Stearate | 5 | 3 |
| | | 500 | 300 |

Formulation C

| | mg/tablet |
|---|---|
| Active ingredient | 100 |
| Lactose | 200 |
| Starch | 50 |
| Povidone | 5 |
| Magnesium stearate | 4 |
| | 359 |

The following formulations, D and E, are prepared by direct compression of the admixed ingredients. The lactose used in formulation E is of the direct compression type (Dairy Crest—"Zeparox").

Formulation D

| | mg/capsule |
|---|---|
| Active Ingredient | 250 |
| Pregelatinised Starch NF15 | 150 |
| | 400 |

Formulation E

| | mg/capsule |
|---|---|
| Active ingredient | 250 |
| Lactose | 150 |
| Avicel | 100 |
| | 500 |

Formulation F (Controlled Release Formulation)

The formulation is prepared by wet granulation of the ingredients (below) with a solution of povidone followed by the addition of magnesium stearate and compression.

| | | mg/tablet |
|---|---|---|
| (a) | Active ingredient | 500 |
| (b) | Hydroxypropylmethylcellulose (Methocel K4M Premium) | 112 |
| (c) | Lactose B.P. | 53 |
| (d) | Povidone B.P.C. | 28 |
| (e) | Magnesium Stearate | 7 |
| | | 700 |

Drug release takes place over a period of about 6–8 hours and is complete after 12 hours.

EXAMPLE 2: CAPSULE FORMULATIONS

Formulation A

A capsule formulation is prepared by admixing the ingredients of Formulation D in Example 1 above and filling into a two-part hard gelatin capsule. Formulation B (infra) is prepared in a similar manner.

Formulation B

| | | mg/capsule |
|---|---|---|
| (a) | Active ingredient | 250 |
| (b) | Lactose B.P. | 143 |
| (c) | Sodium Starch Glycollate | 25 |
| (d) | Magnesium Stearate | 2 |
| | | 420 |

Formulation C

| | | mg/capsule |
|---|---|---|
| (a) | Active ingredient | 250 |
| (b) | Macrogol 4000 BP | 350 |
| | | 600 |

Capsules are prepared by melting the Macrogol 4000 BP, dispersing the active ingredient in the melt and filling the melt into a two-part hard gelatin capsule.

Formulation D

|  | mg/capsule |
| --- | --- |
| Active ingredient | 250 |
| Lecithin | 100 |
| Arachis Oil | 100 |
|  | 450 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b and c using an extruder, followed by spheronisation of the extrudate and drying. The dried pellets are then coated with release-controlling membrane (d) and filled into a two-piece, hard gelatin capsule.

|  |  | mg/capsule |
| --- | --- | --- |
| (a) | Active Ingredient | 250 |
| (b) | Microcrystalline Cellulose | 125 |
| (c) | Lactose BP | 125 |
| (d) | Ethyl Cellulose | 13 |
|  |  | 513 |

All of the above oral formulations A through E are provided with an enteric coating.

EXAMPLE 3: INJECTABLE FORMULATION

Formulation A

| Active ingredient |  | 0.200 g |
| --- | --- | --- |
| Hydrochloric acid solution, 0.1 M | q.s. to pH | 4.0 to 7.0 |
| Sodium hydroxide solution, 0.1 M | q.s. to pH | 4.0 to 7.0 |
| Sterile water | q.s. to | 10 ml |

The active ingredient is dissolved in most of the water (35°–40° C.) and the pH adjusted to between 4.0 and 7.0 with the hydrochloric acid or the sodium hydroxide as appropriate. The batch is then made up to volume with the water and filtered through a sterile micropore filter into a sterile 10 ml amber glass vial (type 1) and sealed with sterile closures and overseals.

Formulation B

| Active ingredient | 0.125 g |
| --- | --- |
| Sterile pyrogen-free, pH7 phosphate buffer q.s. to | 25 ml |

EXAMPLE 4: INTRAMUSCULAR INJECTION

| Active ingredient | 0.20 g |
| --- | --- |
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile microscope filter and sealed in sterile 3 ml amber glass vials (type 1).

EXAMPLE 5: SYRUP

| Active ingredient | 0.2500 g |
| --- | --- |
| Sorbitol Solution | 1.5000 g |
| Glycerol | 2.0000 g |
| Sodium Benzoate | 0.0050 g |
| Flavour, Peach 17.42.3169 | 0.0125 ml |
| Purified Water q.s. to | 5.0000 ml |

The active ingredient is dissolved in a mixture of the glycerol and most of the purified water. An aqueous solution of the sodium benzoate is then added to the solution, followed by addition of the sorbitol solution and finally the flavour. The volume is made up with purified water and mixed well.

EXAMPLE 6: SUPPOSITORY

|  | mg/suppository |
| --- | --- |
| Active ingredient(63 μm)* | 250 |
| Hard Fat, (Witepsol H15 - Dynamit NoBel) | 1770 |
|  | 2020 |

*The active ingredient is used as a powder wherein at least 90% of the particles were of 63μm diameter or less.

One-fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stired to ensure a homogeneous mix. The entire suspension is passed through a 250 μm stainless steel screen and, with continuous stirring, is allowed to cool to 40° C. At a temperature of 38° C. to 40° C., 2.02 g of the mixture is filled into suitable, 2 ml plastic moulds. The suppositories are allowed to cool to room temperature.

EXAMPLE 7: PESSARIES

|  | mg/pessary |
| --- | --- |
| Active ingredient(63 μm) | 250 |
| Anhydrate Dextrose | 380 |
| Potato Starch | 363 |
| Magnesium Stearate | 7 |
|  | 1000 |

The above ingredients are mixed directly and pessaries prepared by direct compression of the resulting mixture.

EXAMPLE 8:
2,6-Diaminopurine-9-β-D-2',3'-dideoxyribofuranoside 2,6-Diaminopurine (9.26 mmoles, 1.39 g) and 2',3'-dideoxythymidine (4.42 mmoles, 1 g) were suspended in 50 ml deionized water containing 0.4 ml 1M $K_2HPO_4$. The pH of the suspension was adjusted to 7.6 with the addition of 0.1M of $KH_2PO_4$. The enzyme catalyst purified from *Escherichia coli*, purine nucleoside phosphorylase (1340 I.U.) and thymidine phosphorylase (4450 I.U.) (Krenitsky et al., *Biochemistry*, 20 3615, 1981 and U.S. Pat. No. 4,381,344) were added and the suspension stirred at 35° C. After 18 hours, an additional 2225 I.U. of thymidine phosphorylase was added. Two days later, the reaction was filtered and the filtrate stored at −20° C. Upon thawing, the suspension was adjusted to a pH of 10.6 with concentrated ammonium hydroxide and chromatographed on a column of Dowex-1-formate resin (2.5×9 cm) with water as the elutant. Fractions containing product were combined and the solvent removed under vacuum. The residue was recrystallised from hot water yielding 2,6-diaminopurine-9-$\beta$-D-2′,3′-dideoxyribofuranoside that analysed as a half hydrate (m.p. 192°).

Anal. Calcd. for $C_{10}H_{14}N_6O_2 \cdot 0.5H_2O$: C, 46.33; H, 5.83; N, 32.41. Found; C, 46.27; H, 5.83; N, 32.39

EXAMPLE 9:
2-Aminopurine-9-$\beta$-D-2′,3′-dideoxyribofuranoside

2′,3′-Dideoxythymidine (4.42 mmoles, 1 g), and 2-aminopurine (8.73 moles, 1.18 g) were combined in 50 ml deionised water containing 0.4 ml 1M $K_2HPO_4$. The suspension had a pH of 7.8. Purine nucleoside phosphorylase (2680 I.U.) and thymidine phosphorylase (4500 I.U.) were added and the reaction stirred at 35° C. On day two, additional thymidine phosphorylase (2225 I.U.) was added and one day later the solids were filtered off and the filtrate stored at −20° C. Upon thawing, solids were removed and combined with the original reaction cake. The filtrate was adjusted to pH 10.5 with concentrated ammonium hydroxide and chromatographed on a Dowex-1-formate column (2.5×11 cm). The product was eluted from the resin with water. After recrystallising from boiling water, a small quantity of 2-amino-9-$\beta$-D-2′,3′-dideoxyribofuranoside was isolated. The remaining solids from the reaction were heated in 25 ml of water to a boil and filtered. This solution was combined with all the liquors from above, the volume reduced, and the solid recrystallised from water. The crystals were combined with the those obtained above to yield a final crop of 2-aminopurine-9-$\beta$-D-2′,3′-dideoxyribofuranoside half hydrate, m.p. 162° C.

Anal. Calcd. for $C_{10}H_{13}N_5O_2 \cdot 0.5H_2O$: C, 49.17; H, 5.78; N, 28.67. Found: C, 48.97; H, 5.80; N, 28.67.

EXAMPLE 10:
6-Methoxypurine-9-$\beta$-D-2′,3′-dideoxyribofuranoside

6-Methoxypurine (8.2 mmoles, 1.23 g) and 2′,3′-dideoxythymidine (4.5 mmoles, 1.0 g) were suspended in 50 ml of a 30 mM potassium phosphate solution with a pH of 7.1. Purine nucleoside phosphorylase (1984 I.U.) and thymidine phosphorylase (7892 I.U.) were added and the reaction incubated at 37° C. After 6 days the reaction mixture was filtered and the filtrate stored frozen at −20° C. Upon thawing, solids were removed by filtration and combined with the original reaction cake. The filtrate was adjusted to pH 10.6 with concentrated ammonium hydroxide and chromatographed on a Dowex-1-formate column (2.5×10 cm). The product was eluted from the resin with water. After removing the water by vacuum, the product was dissolved in 30% n-propanol (v/v) and chromatographed on a column containing P-2 resin (BioRad) (5×90 cm). The product was eluted from the column with 30% n-propanol water (v/v) yielding the title compound after solvent removal (m.p.=157°–165° C.).

Anal. Calc. for $C_{11}H_{14}N_4O_3$: 52.79; H, 5.64; N, 22.39. Found: C, 52.57; H, 5.70; N, 22.32

EXAMPLE 11:
6-Methylthiopurine-9-$\beta$-D-2′,3′-dideoxyribofuranoside

6-Methylthiopurine (7.2 mmoles, 1.2 g) 1.2 g) and 2′,3′-dideoxythymidine (4.5 mmoles, 1 g) were added to 50 ml of deionized water containing 0.4 ml 1M $K_2HPO_4$. The suspension had a pH of 7.7. Thymidine phosphorylase (4450 I.U.) and purine nucleoside phosphorylase (1340 I.U.) were added and the reaction stirred at 37° C. After 4 days the reaction mixture was filtered and the filtrate stored at −20° C. Upon thawing, the solution was filtered and the filtrate chromatographed on a column containing P-2 resin (5×90 cm). The column was eluted with 30% n-propanol/water (v/v). Product-containing fractions were combined and to this was added the original reaction cake. After removal of the solvent the residue was dissolved in 30% methanol/water (v/v). The pH was adjusted to 10.3 with concentrated ammonium hydroxide and chromatographed on a Dowex-1-formate column (2.5×8 cm). The product was eluted with 30% methanol/water (v/v), dried under vacuum and redissolved in 30% n-propanol. The sample was chromatographed on a column containing P-2 resin (5×90 cm) and eluted with 30% n-propanol/water. Product-containing fractions were combined and solvent removed to yield the title compound (m.p.=105° C.).

Anal. calcd. for $C_{11}H_{14}O_2$: C, 49.61; H, 5.30; N, 21.04; S, 12.04. Found: C, 49.63; H, 5.35; N, 20.99; S, 12.04.

EXAMPLE 12: ANTIVIRAL ACTIVITY (a) Feline Leukaemia Virus

Susceptible feline embryo lung fibroblasts (FLF-3) were seeded onto multiwell slides ($10^5$ cells/ml, 0.05 ml/well) with Dulbecco-modified Eagle's essential medium (DME) and incubated at 37° C. overnight. Each of the 32 wells was then infected with 40–60 focus forming units (ffu) of feline leukaemia virus (FeLV) for one hour after which the medium was replaced with fresh DME with varying concentrations of 2,6-diaminopurine-9-$\beta$-D-2′,3′-dideoxyribofuranoside per 4 wells. Concentrations were 0, 1.0, 10, 50, 100, 200 and 400 $\mu$M. After 3 days incubation at 37° C., the cultures were assayed by the indirect fluorescent antigen test for the production of FeLV. Complete absence of FeLV was seen at concentrations of 100 $\mu$M and above, demonstrating total efficacy at these levels of drug. At 50 $\mu$M, 60% inhibition was seen, at 10 $\mu$M, 45% inhibition, and 31% inhibition was noted at 0.1 $\mu$M 2,6-diaminopurine-9-$\beta$-D-2′,3′-dideoxyribofuranoside.

(b) AIDV

The ability of 2,6-diaminopurine-9-$\beta$-D-2′,3′-dideoxyribofuranoside to block infection of cells by AIDV was determined as follows. Cloned T4 positive tetanus specific T helper lymphocytes were infected with a pool of AIDV isolates [at challenge doses of up to 5000 virions/cell] and cell survival after infection was monitored. After 10 days in culture no viral cytopathic effects were seen in infected T cells treated with 10 and 2 $\mu$M 2,6-diaminopurine-9-$\beta$-D-2′,3′-dideoxyribofuranoside, while untreated, infected cells were 8-fold decreased. This protective effect was seen on both days 10 and 13 of the experiment.

(c) Friend Leukaemia virus

The compounds have been tested for retroviral activity against Friend leukaemia virus with the following results.

| Compound | $ED_{50}(\mu M)$ |
| --- | --- |
| 2,6-diaminopurine-9-$\beta$-D-2′,3′dideoxyribofuranoside | 22.35 |
| 2′,3′dideoxyguanosine | 25.89 |

EXAMPLE 13 CYTOTOXICITY

The following compounds were tested for cytotoxic effect at $10^{-4}M$ against human D-98 and mouse L cells. Figures shown are % growth relative to the control.

| Compound | % Growth D-98 | L |
|---|---|---|
| 2,6-diamino-9-(2',3'-dideoxy-β-D-ribofuranosyl)-9H-purine | 97 | 41 |
| 2-amino-9-(2',3'-dideoxy-β-D-ribofuranosyl-9H-purine | 97 | 107 |
| 9-(2',3'-dideoxy-β-D-ribofuranosyl-6-methylthio-9H-purine | 98 | 91 |
| 2',3'-dideoxyguanosine | 87 | 93 |
| 9-(2',3'-dideoxy-β-D-ribofuranosyl-6-methoxy-9H-purine | 92 | 90 |

We claim:

1. 2,6-diaminopurine-9-β-D-2',3'-dideoxyribofuranoside or a pharmaceutically acceptable salt thereof.

* * * * *